US008372055B2

(12) United States Patent
Thornton et al.

(10) Patent No.: US 8,372,055 B2
(45) Date of Patent: Feb. 12, 2013

(54) METHOD OF USING A DEFLECTABLE SUBSELECTING CATHETER

(75) Inventors: Ronan M. Thornton, Co. Galway (IE); David T. Johnson, Co. Galway (IE); Niall F. Duffy, Co. Galway (IE)

(73) Assignee: Medtronic, Inc., Minneapolis, MN (US)

( * ) Notice: Subject to any disclaimer, the term of this patent is extended or adjusted under 35 U.S.C. 154(b) by 467 days.

(21) Appl. No.: 12/606,883

(22) Filed: Oct. 27, 2009

(65) Prior Publication Data

US 2011/0098561 A1  Apr. 28, 2011

(51) Int. Cl.
A61M 25/01 (2006.01)
(52) U.S. Cl. ......... 604/510; 128/898; 600/435; 600/508
(58) Field of Classification Search .................. 600/431, 600/433–435, 425, 508; 604/509, 510, 95.03, 604/96.01–103.13; 607/1–37
See application file for complete search history.

(56) References Cited

U.S. PATENT DOCUMENTS

| | | | |
|---|---|---|---|
| 4,374,382 A | 2/1983 | Markowitz | |
| 4,906,230 A | 3/1990 | Maloney et al. | |
| 5,571,161 A | 11/1996 | Starksen | |
| 5,728,123 A | 3/1998 | Lemelson et al. | |
| 5,882,334 A * | 3/1999 | Sepetka et al. | 604/164.08 |
| 5,916,194 A | 6/1999 | Jacobsen et al. | |
| 6,612,999 B2 | 9/2003 | Brennan et al. | |
| 6,746,469 B2 | 6/2004 | Mouw | |
| 2003/0212446 A1 | 11/2003 | Kaplan et al. | |
| 2004/0054388 A1 | 3/2004 | Osypka | |
| 2004/0073108 A1 | 4/2004 | Saeed et al. | |
| 2004/0116851 A1 | 6/2004 | Johansen et al. | |
| 2004/0186507 A1 | 9/2004 | Hall et al. | |

FOREIGN PATENT DOCUMENTS

| | | |
|---|---|---|
| EP | 0976363 A2 | 2/2000 |
| WO | 9744083 A1 | 11/1997 |
| WO | 0149357 A2 | 7/2001 |

OTHER PUBLICATIONS

Meisel et al. Investigation of Coronary Venous Anatomy by Retrograde Venography in Patients with Malignant Ventricular Tachycardia. Circulation. 104:442-447. 2001.*
International Search Report and Written Opinion from corresponding PCT Application Serial No. PCT/US2010/033391 dated Oct. 13, 2010 (19 pages).
International Preliminary Report on Patentability from international application No. PCT/US2010/033391, dated May 10, 2012, 13 pp.

* cited by examiner

*Primary Examiner* — Parikha Mehta

(57) ABSTRACT

A medical device including, e.g., an implantable medical lead or drug pump catheter, a guide member, or a sheath is delivered to a target location within a patient via a catheter capable of subselecting vessels or other cavities, passages, or the like within the patient's body. The catheter employs an inflatable member that, when actuated, acts to deflect a medical device to direct the device into a vessel or other cavity, passage, or the like branching off of, e.g., a vessel in which the catheter is arranged. In some examples, the inflatable member acts to deflect the delivery catheter, which in turn necessarily deflects the implantable medical device arranged therein. In other examples, the inflatable member acts to deflect the medical device to turn the device into a vessel or other cavity, passage, or the like branching off of the vessel in which the catheter is arranged.

7 Claims, 9 Drawing Sheets

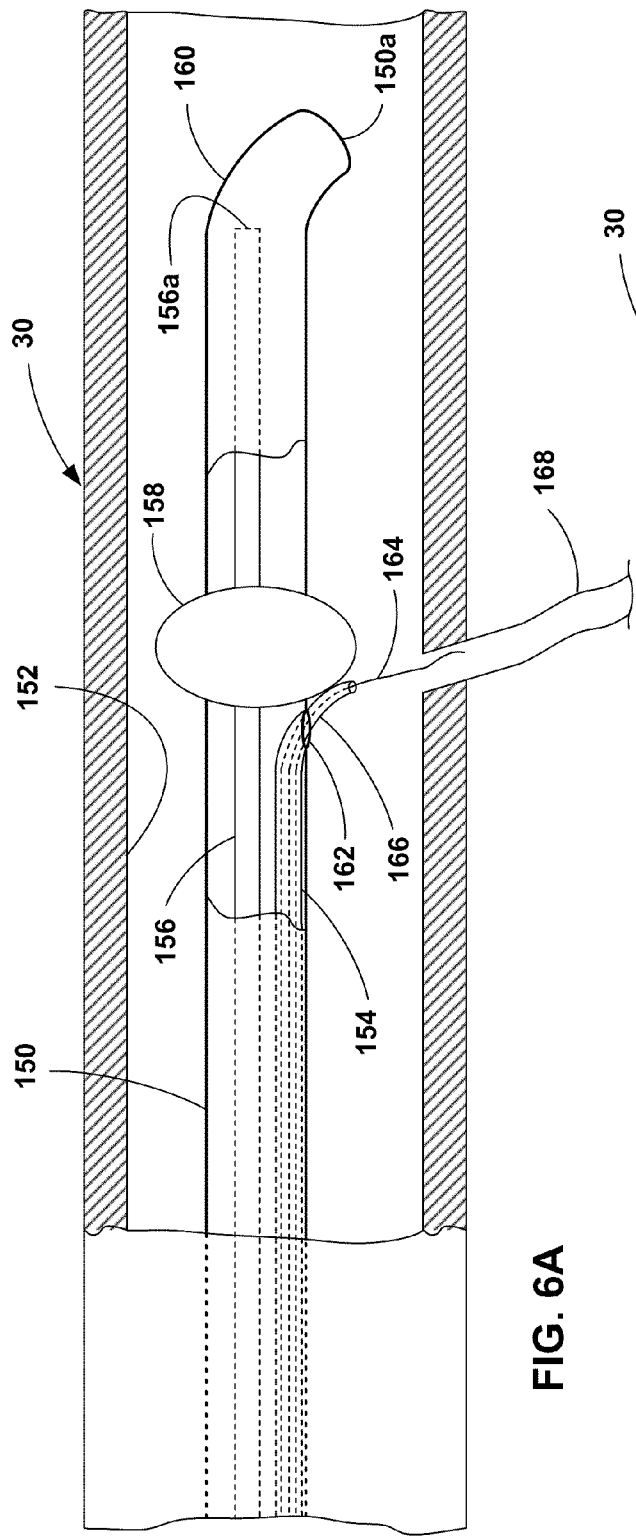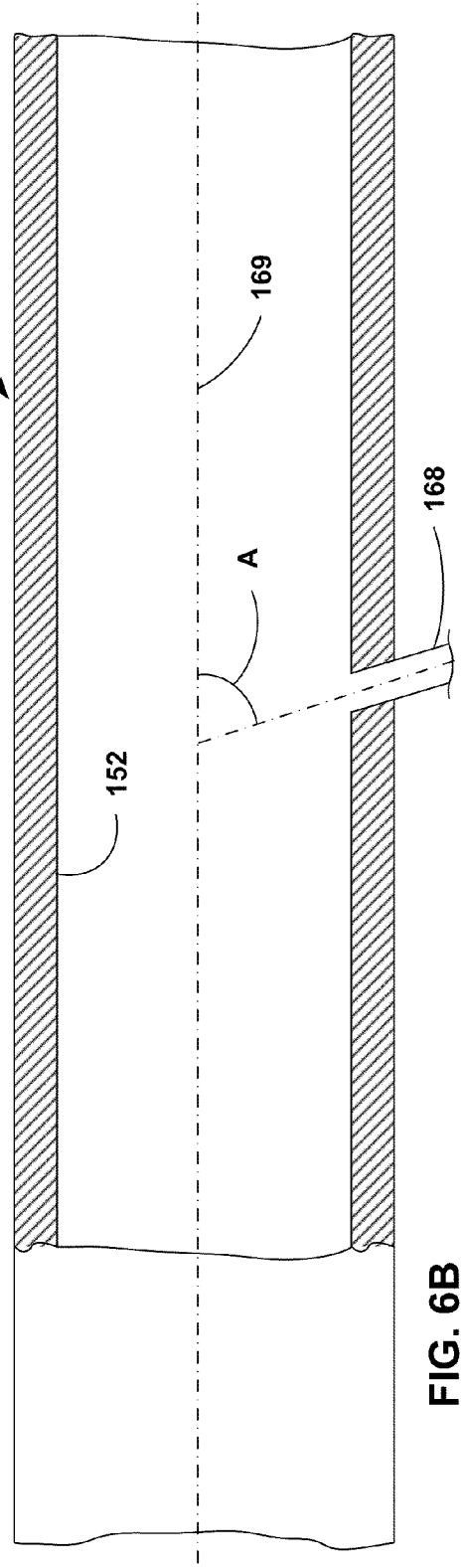

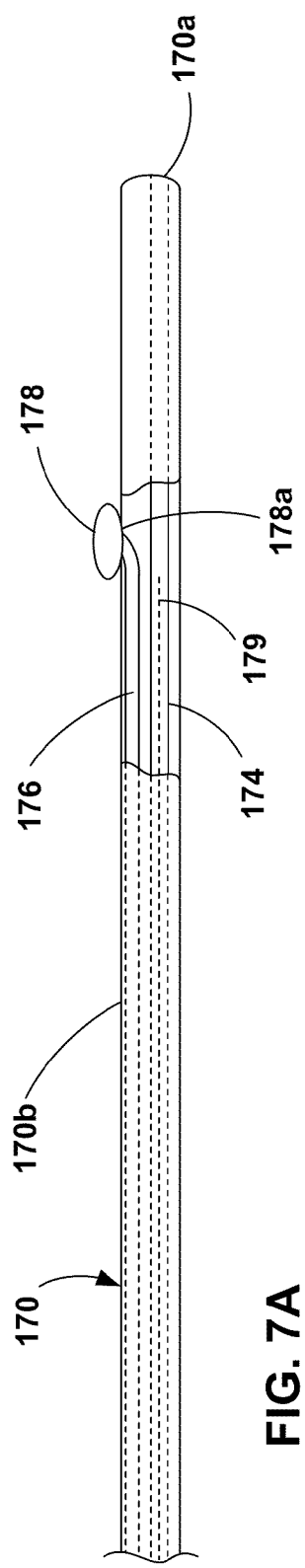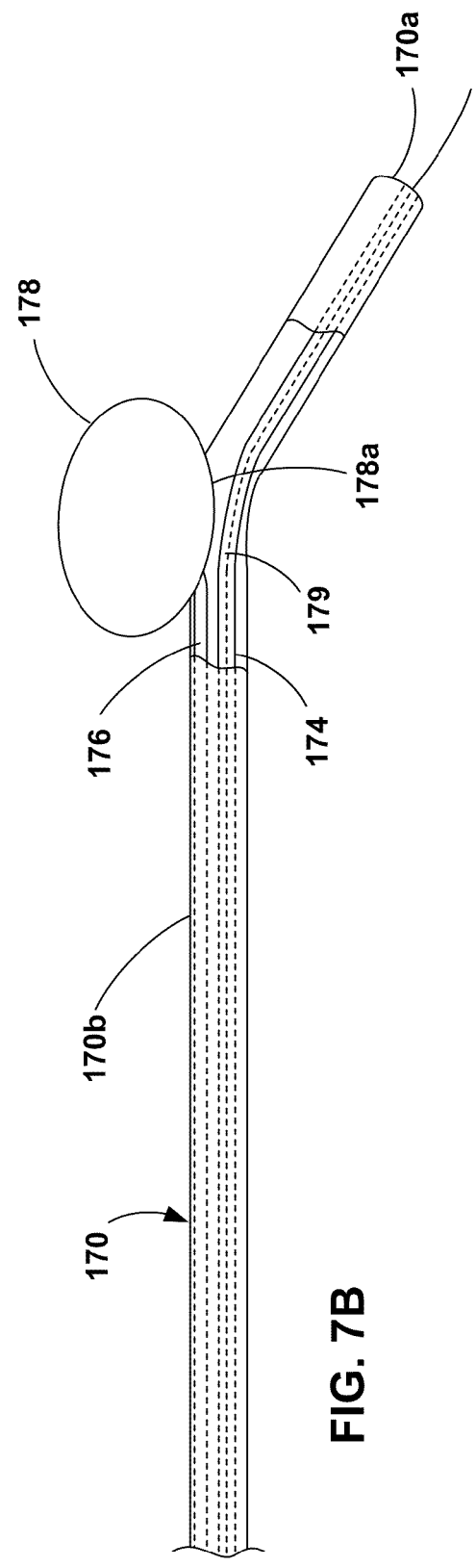

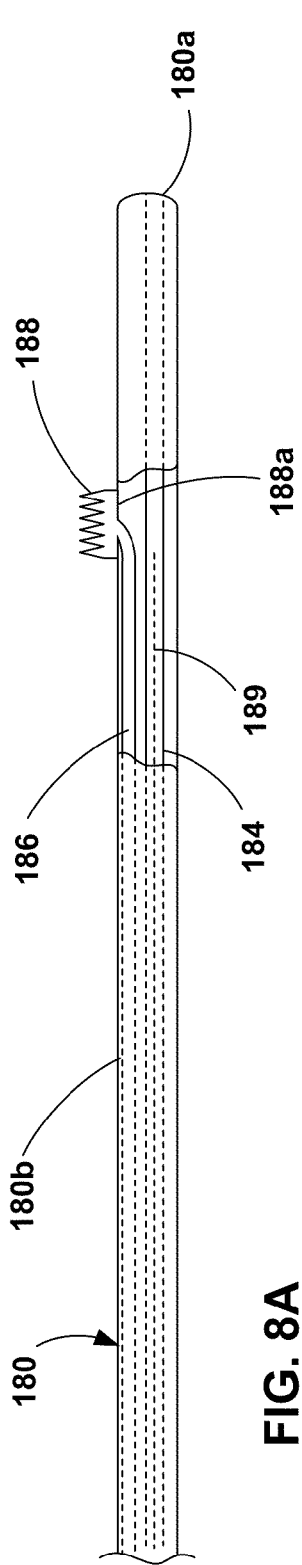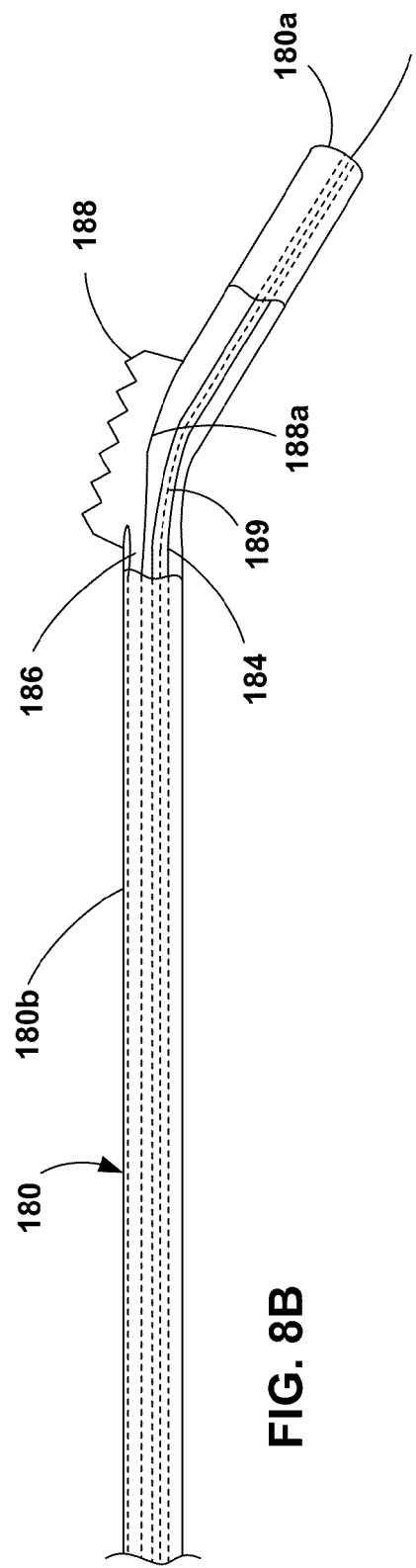

METHOD OF USING A DEFLECTABLE SUBSELECTING CATHETER

TECHNICAL FIELD

The disclosure relates to implantable medical devices, and, more particularly, to subcutaneous placement of components thereof.

BACKGROUND

A variety of implantable medical devices for delivering a therapy and/or monitoring a physiological condition have been clinically implanted or proposed for clinical implantation in patients. Implantable medical devices may deliver electrical stimulation or fluid therapy to, and/or monitor conditions associated with, the heart, muscle, nerve, brain, stomach or other organs or tissue, as examples. Some implantable medical devices may employ one or more elongated electrical leads carrying stimulation electrodes, sense electrodes, and/ or other sensors. Implantable medical leads may be configured to allow electrodes or other sensors to be positioned at desired locations for delivery of stimulation or sensing. For example, electrodes or sensors may be carried at a distal portion of a lead. A proximal portion of the lead may be coupled to an implantable medical device housing, which may contain circuitry such as stimulation generation and/or sensing circuitry.

Implantable medical devices, such as cardiac pacemakers or implantable cardioverter-defibrillators, for example, provide therapeutic electrical stimulation to the heart via electrodes carried by one or more implantable leads. The electrical stimulation may include signals such as pulses or shocks for pacing, cardioversion or defibrillation. In some cases, an implantable medical device may sense intrinsic depolarizations of the heart, and control delivery of stimulation signals to the heart based on the sensed depolarizations. Upon detection of an abnormal rhythm, such as bradycardia, tachycardia or fibrillation, an appropriate electrical stimulation signal or signals may be delivered to restore or maintain a more normal rhythm. For example, in some cases, an implantable medical device may deliver pacing pulses to the heart of the patient upon detecting tachycardia or bradycardia, and deliver cardioversion or defibrillation shocks to the heart upon detecting tachycardia or fibrillation.

Placing implantable medical devices, such as implantable medical leads, within patients often requires guiding the leads through a series of vessels or other cavities within the body. Manipulating the leads to follow the contours of the vessels is often difficult and time consuming. It is particularly challenging and, in some cases, impossible to direct the leads into branching vessels or other cavities that take-off of a primary path at a relatively large acute angle. For example, it may be particularly challenging to direct an implantable medical lead into a vessel that branches off of the coronary sinus, as may be desired for placement of the lead for left-ventricular pacing and/or sensing.

SUMMARY

In general, examples disclosed herein are directed to techniques for delivering medical devices, e.g., an implantable medical lead or drug pump catheter, a guide member, or a sheath via a delivery catheter capable of subselecting vessels or other cavities, passages, or the like within a patient's body. In general, a delivery catheter employs an inflatable member that, when actuated, acts to deflect a medical device to direct the device into a vessel or other cavity, passage, or the like branching off of, e.g. a vessel in which the catheter is arranged. In some examples, the inflatable member acts to deflect the delivery catheter, which in turn necessarily deflects the medical device arranged therein. In other examples, the inflatable member acts to deflect the medical device as the device is advanced from the catheter to turn the device into the vessel or other cavity, passage, or the like branching off of the vessel in which the catheter is arranged.

In one example, a system includes a delivery catheter, a medical device, and an inflatable member. The delivery catheter includes a proximal end and a distal end. The medical device is configured to be received within the delivery catheter. The inflatable member is arranged on a distal portion of the delivery catheter and configured to deflect a distal end of the medical device as the medical device is advanced out of the distal portion of the delivery catheter.

In another example, a method includes delivering a catheter comprising an inflatable member through a vessel within a patient. A medical device is advanced through the catheter. The inflatable member is expanded to deflect the medical device at an acute angle with respect to a longitudinal axis of the vessel as the medical device is advanced through the catheter.

The details of one or more examples are set forth in the accompanying drawings and the description below. Other features, objects, and advantages of the disclosure will be apparent from the description and drawings, and from the claims.

BRIEF DESCRIPTION OF DRAWINGS

FIG. 6A is schematic illustration of an example delivery catheter arranged in the primary vein of the coronary sinus of a patient.

FIG. 6B illustrates the angle of a secondary vein of the coronary sinus with respect to the primary vein thereof.

FIGS. 7A and 7B are schematic illustrations of another example delivery catheter.

FIGS. 8A and 8B are schematic illustrations of another example delivery catheter.

DETAILED DESCRIPTION

Figure 1:
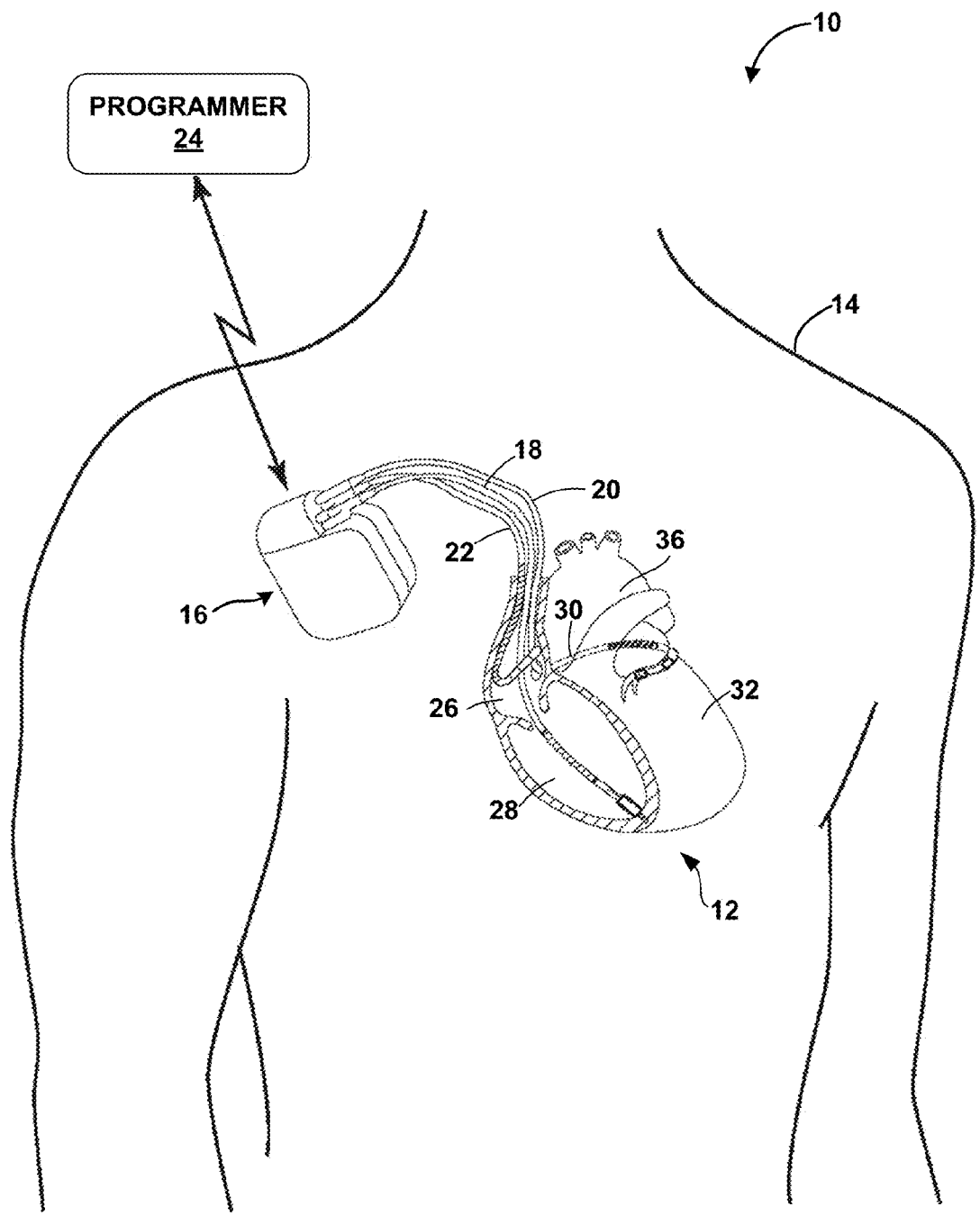
FIG. 1 is a conceptual drawing illustrating an example system that includes an implantable medical device (IMD) coupled to implantable medical leads.

FIG. 1 is a conceptual diagram illustrating an example system 10 that may be used for sensing of physiological parameters of patient 14 and/or to provide therapy to heart 12 of patient 14. Therapy system 10 includes IMD 16, which is coupled to leads 18, 20, and 22, and programmer 24. IMD 16 may be, for example, an implantable pacemaker, cardioverter, and/or defibrillator that provides electrical signals to heart 12 via electrodes coupled to one or more of leads 18, 20, and 22. Patient 14 is ordinarily, but not necessarily, a human patient.

Leads 18, 20, 22 extend into the heart 12 of patient 16 to sense electrical activity of heart 12 and/or deliver electrical stimulation to heart 12. In the example shown in FIG. 1, right ventricular (RV) lead 18 extends through one or more veins (not shown), the superior vena cava (not shown), and right atrium 26, and into right ventricle 28. Left ventricular (LV) coronary sinus lead 20 extends through one or more veins, the vena cava, right atrium 26, and into the coronary sinus 30 to a region adjacent to the free wall of left ventricle 32 of heart 12. Right atrial (RA) lead 22 extends through one or more veins and the vena cava, and into the right atrium 26 of heart 12.

In order to properly position leads 18, 20, 22 within heart 12 of patient 14, it is often necessary for the implanting physician to navigate a multitude of twists and turns within the vessels or other parts of the patients body through which the leads are guided to their destination. In the example of FIG. 1, LV lead 20 must be, e.g., passed through a vein into right atrium 26 and then turn into coronary sinus 30. In such examples, it is also advantageous for lead 20 to be able to subselect one of the many smaller veins branching off from the primary vein of coronary sinus 30 in which lead 20 is shown in FIG. 1.

The precise placement of lead 20 in one of the veins of coronary sinus 30 may be necessary in order to, e.g., avoid secondary stimulation of nerves that lie adjacent or otherwise in the region of the coronary sinus. The left phrenic nerve is one nerve that it may be desirable to avoid stimulating with electrodes connected to lead 20 in coronary sinus 30. The phrenic nerve arises from the third, fourth, and fifth cervical spinal nerves in humans and passes over the pericardium of the left ventricle. The nerve functions to, inter alia, contract the diaphragm. As such, uncontrolled or unintended stimulation may adversely affect a patient's ability to breathe.

Subselecting vessels off of primary vein of coronary sinus 30 is often difficult because the take-off angle of the vessels from the primary vein is often severe. It is not uncommon, e.g., for a vessel branching off of the primary vein of coronary sinus 30 to have a take-off angle in a range from 60 to more than 90 degrees with respect to, e.g., a longitudinal axis of the coronary sinus (see FIG. 6B).

As described in detail with reference to FIGS. 7-9, examples disclosed herein are directed to techniques for delivering medical devices, e.g. an implantable medical lead or a drug pump catheter, via a delivery catheter capable of subselecting vessels or other cavities, passages, or the like within a patient's body. In general, a delivery catheter employs an inflatable member that, when actuated, acts to deflect a medical device within the catheter in order to direct the device into a vessel or other cavity, passage, or the like branching off of the path along which the catheter is arranged. The medical device may include, e.g., an implantable medical lead, drug delivery catheter, guide member, e.g. guide wire, or a sheath. In some examples, the inflatable member acts to deflect the delivery catheter, which in turn necessarily deflects the medical device arranged therein. In other examples, the inflatable member acts to deflect the medical device as the device is advanced from the catheter to turn the device away from the path along which the catheter is arranged.

Referring again to FIG. 1, system 10 may, in some examples, additionally or alternatively include one or more leads or lead segments (not shown in FIG. 1) that deploy one or more electrodes within the vena cava or other vein. These electrodes may allow alternative electrical sensing configurations that may provide improved or supplemental sensing in some patients. Furthermore, in some examples, therapy system 10 may include temporary or permanent epicardial or subcutaneous leads, instead of or in addition to leads 18, 20 and 22. Such leads may be used for one or more of cardiac sensing, pacing, or cardioversion/defibrillation.

IMD 16 may sense electrical signals attendant to the depolarization and repolarization of heart 12 via electrodes (not shown in FIG. 1) coupled to at least one of the leads 18, 20, 22. In some examples, IMD 16 provides pacing pulses to heart 12 based on the electrical signals sensed within heart 12. The configurations of electrodes used by IMD 16 for sensing and pacing may be unipolar or bipolar. IMD 16 may detect arrhythmia of heart 12, such as tachycardia or fibrillation of ventricles 28 and 32, and may also provide defibrillation therapy and/or cardioversion therapy via electrodes located on at least one of the leads 18, 20, 22. In some examples, IMD 16 may be programmed to deliver a progression of therapies, e.g., pulses with increasing energy levels, until a fibrillation of heart 12 is stopped. IMD 16 detects fibrillation employing any of a number of known fibrillation detection techniques.

One or more of leads 18, 20 and 22 may be delivered to heart 12 of patient 14 with a deflectable catheter capable of subselecting vessels or other cavities, passages, or the like within the body of the patient. In some examples, one or more of leads 18, 20 and 22 of IMD 16 are delivered via a catheter that includes a inflatable member that, when actuated, acts to deflect the lead received within the catheter in order to direct the lead out of an aperture in the catheter, and thereby into a vessel or other cavity, passage, or the like branching off of the path along which the catheter is arranged. For example, LV lead 20 may be passed within the delivery catheter through a vein into right atrium 26 and then into coronary sinus 30. Once in the coronary sinus 30, the inflatable member may be actuated to deflect lead 20 as it is advanced out of an aperture in the catheter, thereby directing the lead into one of the many smaller veins branching off from the primary vein of the coronary sinus 30. In other examples, the inflatable member acts to deflect the delivery catheter itself, which, in turn, necessarily deflects one or more of leads 18, 20 and 22 arranged therein.

Programmer 24 shown in FIG. 1 may be a handheld computing device, computer workstation, or networked computing device. Programmer 24 may include a user interface that receives input from a user. The user interface may include, for example, a keypad and a display, which may for example, be a cathode ray tube (CRT) display, a liquid crystal display (LCD) or light emitting diode (LED) display. The keypad may take the form of an alphanumeric keypad or a reduced set of keys associated with particular functions. Programmer 24 can additionally or alternatively include a peripheral pointing device, such as a mouse, via which a user may interact with the user interface. In some embodiments, a display of programmer 24 may include a touch screen display, and a user may interact with programmer 24 via the display. It should be noted that the user may also interact with programmer 24 remotely via a networked computing device.

A user, such as a physician, technician, surgeon, electrophysiologist, or other clinician, may interact with programmer 24 to communicate with IMD 16. For example, the user may interact with programmer 24 to retrieve physiological or diagnostic information from IMD 16. A user may also interact with programmer 24 to program IMD 16, e.g., select values for operational parameters of the IMD.

For example, the user may use programmer 24 to retrieve information from IMD 16 regarding the rhythm of heart 12, trends therein over time, or arrhythmic episodes. As another example, the user may use programmer 24 to retrieve information from IMD 16 regarding other sensed physiological parameters of patient 14, such as intracardiac or intravascular pressure, activity, posture, respiration, or thoracic impedance. As another example, the user may use programmer 24 to retrieve information from IMD 16 regarding the performance or integrity of IMD 16 or other components of system 10, such as leads 18, 20 and 22, or a power source of IMD 16. In some examples, this information may be presented to the user as an alert.

The user may use programmer 24 to program a therapy progression, select electrodes used to deliver defibrillation pulses, select waveforms for the defibrillation pulse, or select or configure a fibrillation detection algorithm for IMD 16. The user may also use programmer 24 to program aspects of other therapies provided by IMD 16, such as cardioversion or pacing therapies. In some examples, the user may activate certain features of IMD 16 by entering a single command via programmer 24, such as depression of a single key or combination of keys of a keypad or a single point-and-select action with a pointing device.

IMD 16 and programmer 24 may communicate via wireless communication using any number of known techniques. Examples of communication techniques may include, for example, low frequency or radiofrequency (RF) telemetry, but other techniques are also contemplated. In some examples, programmer 24 may include a programming head that may be placed proximate to the patient's body near the IMD 16 implant site in order to improve the quality or security of communication between IMD 16 and programmer 24.

Figure 2:
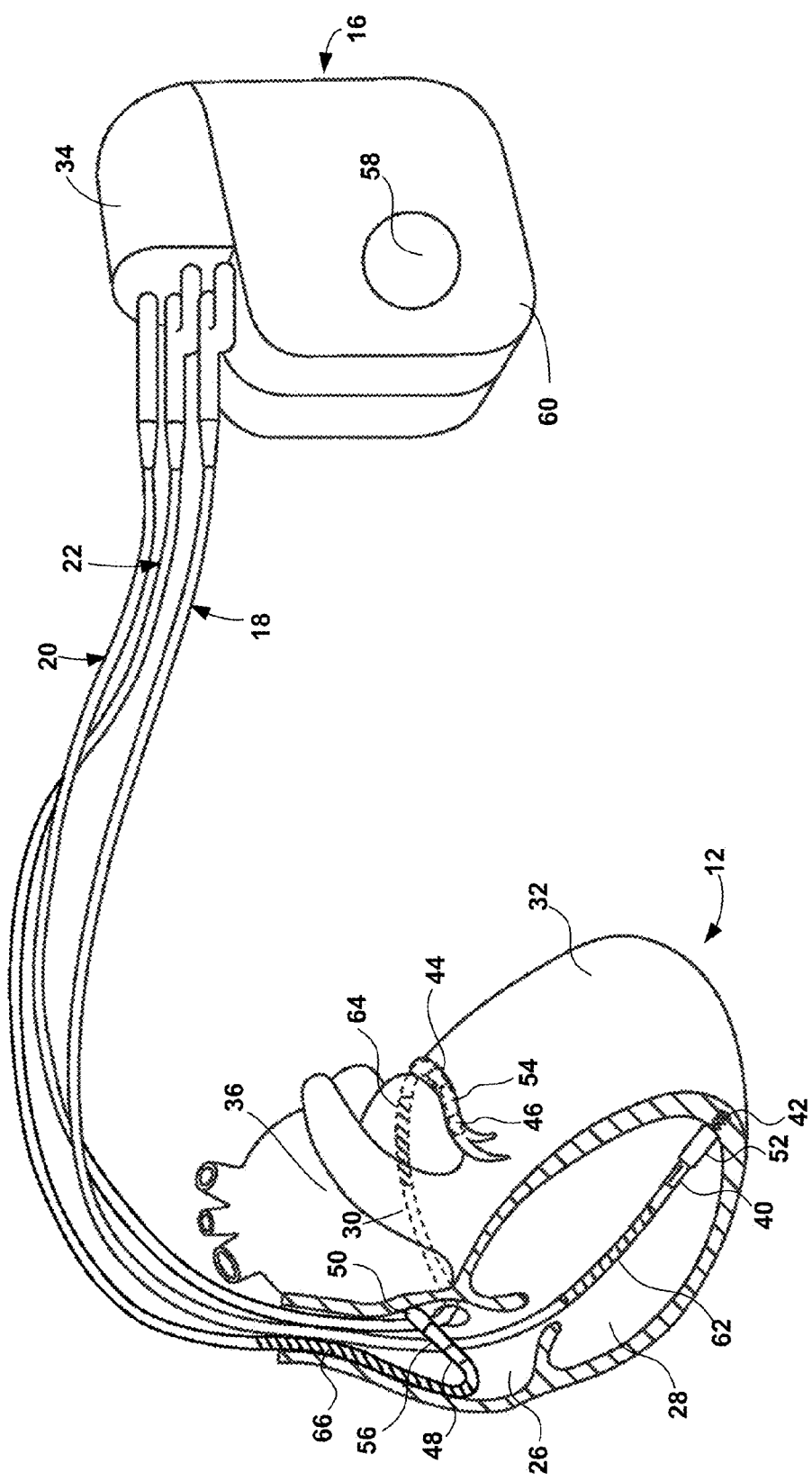
FIG. 2 is a conceptual drawing illustrating the example IMD and leads of FIG. 1 in conjunction with a heart.

FIG. 2 is a conceptual diagram illustrating IMD 16 and leads 18, 20 and 22 of therapy system 10 in greater detail. Leads 18, 20, 22 may be electrically coupled to a signal generator, e.g., stimulation generator, and a sensing module of IMD 16 via connector block 34. In some examples, proximal ends of leads 18, 20, 22 may include electrical contacts that electrically couple to respective electrical contacts within connector block 34 of IMD 16. In addition, in some examples, leads 18, 20, 22 may be mechanically coupled to connector block 34 with the aid of set screws, connection pins, snap connectors, or another suitable mechanical coupling mechanism.

Each of the leads 18, 20, 22 includes an elongated insulative lead body, which may carry a number of concentric coiled conductors separated from one another by tubular insulative sheaths. Bipolar electrodes 40 and 42 are located adjacent to a distal end of lead 18 in right ventricle 28. In addition, bipolar electrodes 44 and 46 are located adjacent to a distal end of lead 20 in coronary sinus 30 and bipolar electrodes 48 and 50 are located adjacent to a distal end of lead 22 in right atrium 26. In the illustrated example, there are no electrodes located in left atrium 36. However, other examples may include electrodes in left atrium 36.

Electrodes 40, 44 and 48 may take the form of ring electrodes, and electrodes 42, 46 and 50 may take the form of extendable helix tip electrodes mounted retractably within insulative electrode heads 52, 54 and 56, respectively. In other embodiments, one or more of electrodes 42, 46 and 50 may take the form of small circular electrodes at the tip of a tined lead or other fixation element. Leads 18, 20, 22 also include elongated electrodes 62, 64, 66, respectively, which may take the form of a coil. Each of the electrodes 40, 42, 44, 46, 48, 50, 62, 64 and 66 may be electrically coupled to a respective one of the coiled conductors within the lead body of its associated lead 18, 20, 22, and thereby coupled to respective ones of the electrical contacts on the proximal end of leads 18, 20 and 22.

In some examples, as illustrated in FIG. 2, IMD 16 includes one or more housing electrodes, such as housing electrode 58, which may be formed integrally with an outer surface of hermetically-sealed housing 60 of IMD 16 or otherwise coupled to housing 60. In some examples, housing electrode 58 is defined by an uninsulated portion of an outward facing portion of housing 60 of IMD 16. Other division between insulated and uninsulated portions of housing 60 may be employed to define two or more housing electrodes. In some examples, housing electrode 58 comprises substantially all of housing 60. As described in further detail with reference to FIG. 4, housing 60 may enclose a signal generator that generates therapeutic stimulation, such as cardiac pacing pulses and defibrillation shocks, as well as a sensing module for monitoring the rhythm of heart 12.

IMD 16 may sense electrical signals attendant to the depolarization and repolarization of heart 12 via electrodes 40, 42, 44, 46, 48, 50, 62, 64 and 66. The electrical signals are conducted to IMD 16 from the electrodes via the respective leads 18, 20, 22. IMD 16 may sense such electrical signals via any bipolar combination of electrodes 40, 42, 44, 46, 48, 50, 62, 64 and 66. Furthermore, any of the electrodes 40, 42, 44, 46, 48, 50, 62, 64 and 66 may be used for unipolar sensing in combination with housing electrode 58. The sensed electrical signals may be processed as the EMG signal by IMD 16.

Any combination of electrodes 40, 42, 44, 46, 48, 50, 58, 62, 64 and 66 may be considered a sensing configuration that has one or more electrodes. In some examples, a sensing configuration may be a bipolar electrode combination on the same lead, such as electrodes 40 and 42 of lead 18. On one lead having three electrodes, there may be three different sensing configurations available to IMD 16. These sensing configurations are, for the example of lead 18, tip electrode 42 and ring electrode 40, tip electrode 42 and elongated electrode 62, and ring electrode 40 and elongated electrode 62. These sensing configurations may be considered near-field configurations. However, some embodiments may utilize sensing configurations having electrodes of two different leads. Furthermore, a sensing configuration may utilize housing electrode 58 as one of the electrodes. These sensing configurations utilizing at least one electrode away from heart 12, e.g., elongated electrode 62 and housing electrode 58 or housing electrode 58 and another housing electrode (not shown), may be considered far-field configurations. In any sensing configuration, the polarity of each electrode in the sensing configuration may be configured as appropriate for the application of the sensing configuration.

In some examples, IMD 16 delivers pacing pulses via bipolar combinations of electrodes 40, 42, 44, 46, 48 and 50 to produce depolarization of cardiac tissue of heart 12. In some examples, IMD 16 delivers pacing pulses via any of electrodes 40, 42, 44, 46, 48 and 50 in combination with housing electrode 58 in a unipolar configuration. Furthermore, IMD 16 may deliver cardioversion or defibrillation pulses to heart 12 via any combination of elongated electrodes 62, 64, 66, and housing electrode 58. Electrodes 58, 62, 64, 66 may also be used to deliver cardioversion pulses, e.g., a responsive therapeutic shock, to heart 12. Electrodes 62, 64, 66 may be fabricated from any suitable electrically conductive material, such as, but not limited to, platinum, platinum alloy or other materials known to be usable in implantable defibrillation electrodes.

As described above, one or more of leads 18, 20 and 22 may be delivered to heart 12 of patient 14 with a catheter according to the examples disclosed herein. The techniques disclosed herein employ a delivery catheter that is capable of subselecting vessels or other cavities, passages, or the like within the body of the patient. For example, LV lead 20 may be passed within a delivery catheter through a vein into right atrium 26 and then into coronary sinus 30 to arrange bipolar electrodes 44 and 46 in a position to stimulate left ventricle 32 of heart 12. The delivery catheter is configured to subselect a vessel branching off of the primary vein or coronary sinus 30 to, for example, avoid stimulating one or more nerves adjacent to the primary vein of coronary sinus 30, e.g., the left phrenic nerve. More generally, subselecting vessels that branch off of a primary vessel, e.g. coronary sinus 30, may allow for identification of a more efficacious location in terms of the timing or completeness of contraction of heart 12, instead of or in addition to avoiding extraneous nerve stimulation. In some examples, lead 20 of IMD 16 is delivered via a catheter that includes an inflatable member that, when actuated, acts to deflect the lead as it is advanced out of an aperture in the catheter, thereby directing the lead into the vessel that branches off of coronary sinus 30. In other examples, the inflatable member acts to deflect the delivery catheter itself, which in turn necessarily deflects lead 20 arranged therein.

The configuration of therapy system 10 illustrated in FIGS. 1 and 2 is merely one example. In other examples, a therapy system may include epicardial leads and/or patch electrodes instead of or in addition to the transvenous leads 18, 20, 22 illustrated in FIG. 1. Further, IMD 16 need not be implanted within patient 14. In examples in which IMD 16 is not implanted in patient 14, IMD 16 may deliver defibrillation pulses and other therapies to heart 12 via percutaneous leads that extend through the skin of patient 14 to a variety of positions within or outside of heart 12.

In addition, in other examples, a therapy system may include any suitable number of leads coupled to IMD 16, and each of the leads may extend to any location within or proximate to heart 12. For example, other examples of therapy systems may include three transvenous leads located as illustrated in FIGS. 1 and 2, and an additional lead located within or proximate to left atrium 36. As another example, other examples of therapy systems may include a single lead that extends from IMD 16 into right atrium 26 or right ventricle 28, or two leads that extend into a respective one of the right ventricle 26 and right atrium 26.

Although delivery techniques according to this disclosure are described in the context of cardiac pacing/sensing leads, the examples disclosed herein may also be employed to place other types of implantable medical devices. For example, a delivery catheter capable of subselecting vessels or other cavities, passages, or the like within the body of the patient as described herein may be employed to deliver neurostimulation leads for spinal cord, gastric, pelvic floor, or deep brain stimulation applications. Additionally, the examples disclosed herein may be used to deliver catheters included in implantable fluid delivery systems, e.g. implantable drug pumps.

Figure 3:
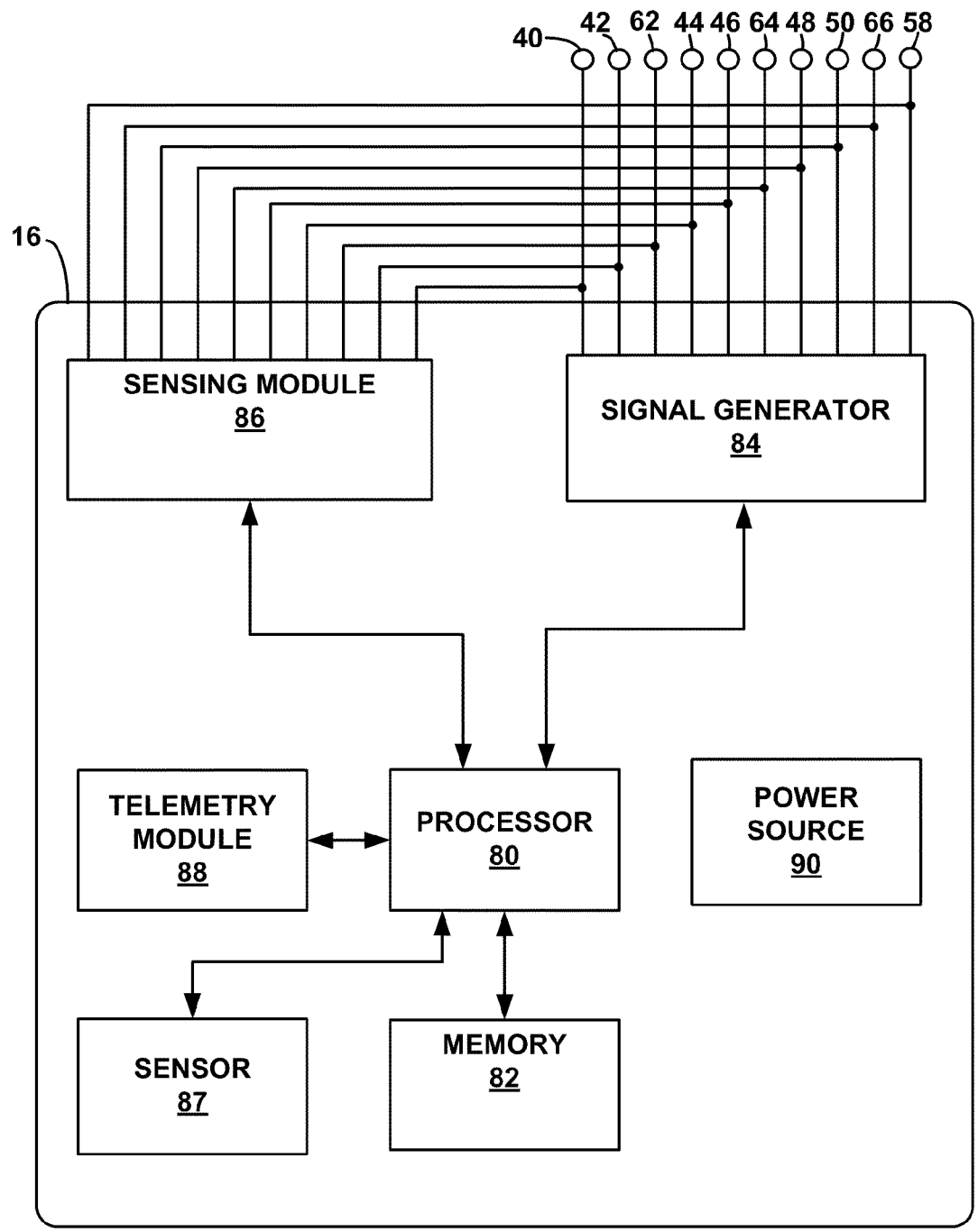
FIG. 3 is a functional block diagram illustrating an example configuration of the IMD of FIG. 1.

FIG. 3 is a functional block diagram illustrating an example configuration of IMD 16. In the illustrated example, IMD 16 includes a processor 80, memory 82, signal generator 84, sensing module 86, sensor 87, telemetry module 88, and power source 90. Memory 82 includes computer-readable instructions that, when executed by processor 80, cause IMD 16 and processor 80 to perform various functions attributed to IMD 16 and processor 80 herein. Memory 82 may include any volatile, non-volatile, magnetic, optical, or electrical media, such as a random access memory (RAM), read-only memory (ROM), non-volatile RAM (NVRAM), electrically-erasable programmable ROM (EEPROM), flash memory, or any other digital or analog media.

Processor 80 may include any one or more of a microprocessor, a controller, a digital signal processor (DSP), an application specific integrated circuit (ASIC), a field-programmable gate array (FPGA), or equivalent discrete or analog logic circuitry. In some examples, processor 80 may include multiple components, such as any combination of one or more microprocessors, one or more controllers, one or more DSPs, one or more ASICs, or one or more FPGAs, as well as other discrete or integrated logic circuitry. The functions attributed to processor 80 herein may be embodied as software, firmware, hardware or any combination thereof.

Processor 80 controls signal generator 84 to deliver stimulation therapy to heart 12 according to a selected one or more of therapy programs, which may be stored in memory 82. For example, processor 80 may control signal generator 84 to deliver electrical pulses with the amplitudes, pulse widths, frequency, or electrode polarities specified by the selected one or more therapy programs.

Signal generator 84 is electrically coupled to electrodes 40, 42, 44, 46, 48, 50, 58, 62, 64, and 66, e.g., via conductors of the respective lead 18, 20, 22, or, in the case of housing electrode 58, via an electrical conductor disposed within housing 60 of IMD 16. Signal generator 84 is configured to generate and deliver electrical stimulation therapy to heart 12. For example, signal generator 84 may deliver defibrillation shocks as therapy to heart 12 via at least two electrodes 58, 62, 64, 66. Signal generator 84 may deliver pacing pulses via ring electrodes 40, 44, 48 coupled to leads 18, 20, and 22, respectively, and/or helical electrodes 42, 46, and 50 of leads 18, 20, and 22, respectively. As pacing heart 12 of patient 14 with electrodes 44 and 46 of lead 20 arranged in coronary sinus 30 may undesirably excite adjacent nerve tissue, e.g. the left phrenic nerve, examples disclosed employ a catheter capable of subselecting vessels or other cavities, passages, or the like to deliver lead 20 to a vessel branching off of the primary vein of the coronary sinus. More generally, subselecting vessels that branch off of a primary vessel may allow for identification of a more efficacious location in terms of the timing or completeness of contraction of heart 12, instead of or in addition to avoiding extraneous nerve stimulation. In some examples, signal generator 84 delivers pacing, cardioversion, or defibrillation stimulation in the form of electrical pulses. In other examples, signal generator may deliver one or more of these types of stimulation in the form of other signals, such as sine waves, square waves, or other substantially continuous time signals.

Signal generator 84 may include a switch module, and processor 80 may use the switch module to select, e.g., via a data/address bus, which of the available electrodes are used to deliver defibrillation pulses or pacing pulses. The switch module may include a switch array, switch matrix, multiplexer, or any other type of switching device suitable to selectively couple stimulation energy to selected electrodes.

Electrical sensing module 86 monitors signals from at least one of electrodes 40, 42, 44, 46, 48, 50, 58, 62, 64, and 66 in order to monitor electrical activity of heart 12. Electrical sensing module 86 may also include a switch module to select which of the available electrodes are used to sense the heart activity. In some examples, processor 80 selects the electrodes that function as sense electrodes, or the sensing configuration, via the switch module within electrical sensing module 86, e.g., by providing signals via a data/address bus.

In some examples, electrical sensing module 86 includes multiple detection channels, each of which comprise an amplifier. Each sensing channel detects electrical activity in respective chamber of heart 12, and may be configured to detect either R-waves or P-waves. In some examples, electrical sensing module 86 or processor 80 includes an analog-to-digital converter for digitizing the signal received from a sensing channel for electrogram signal processing by processor 80. In response to the signals from processor 80, the switch module within electrical sensing module 86 couples the outputs from the selected electrodes to one of the detection channels or the analog-to-digital converter.

During pacing, escape interval counters maintained by processor 80 may be reset upon sensing of R-waves and P-waves with respective detection channels of electrical sensing module 86. Signal generator 84 may include pacer output circuits that are coupled, e.g., selectively by a switching module, to any combination of electrodes 40, 42, 44, 46, 48, 50, 58, 62, 64, and 66 appropriate for delivery of a bipolar or unipolar pacing pulse to one or more of the chambers of heart 12. Processor 80 may control signal generator 84 to deliver a pacing pulse to a chamber upon expiration of an escape interval. Processor 80 may reset the escape interval counters upon the generation of pacing pulses by stimulation generator 84, or detection of an intrinsic depolarization in a chamber, and thereby control the basic timing of cardiac pacing functions. The escape interval counters may include P-P, V-V, RV-LV, A-V, A-RV, or A-LV interval counters, as examples. The value of the count present in the escape interval counters when reset by sensed R-waves and P-waves may be used by processor 80 to measure the durations of R-R intervals, P-P intervals, P-R intervals and R-P intervals. Processor 80 may use the count in the interval counters to detect a tachyarrhythmia event, such as an atrial or ventricular fibrillation or tachycardia and/or detect a heart rate, such as an atrial rate or ventricular rate.

Processor 80 may also derive other physiological parameters from signals sensed via electrical sensing module 86. For example, processor 80 may establish one or more indicators of ejection fraction and/or heart failure status from electrical signals sensed via electrical sensing module 86. In particular, impedance signals may be used to determine flow or pressure, which may indicate ejection fraction and/or heart failure status.

IMD 16 also includes one or more sensors 87 separate from electrodes 40, 42, 44, 46, 48, 50, 58, 62, 64 and 66. Via a signal generated by sensor 87, processor 80 monitors physiological parameters indicative of cardiac contraction, autonomic tone, heart failure, and/or ejection fraction. Examples of sensors 87 that generate a signal indicative of cardiac contraction include a intracardiac or intravascular pressure sensor, an accelerometer or other sensor capable of detecting heart or blood sounds, vibrations, or motion, an optical or ultrasonic sensor capable of detecting changes in flow associated with cardiac contractions, or an optical sensor capable of detecting oxygen saturation changes associated with cardiac contractions. In some examples, processor 80 detects cardiac contractions based on signals from one or more sensors 87, and detects arrhythmias based on the detected cardiac contractions.

Telemetry module 88 includes any suitable hardware, firmware, software or any combination thereof for communicating with another device, such as programmer 24 (FIG. 1). Under the control of processor 80, telemetry module 88 may receive downlink telemetry from and send uplink telemetry to programmer 24 with the aid of an antenna, which may be internal and/or external. Processor 80 may provide the data to be uplinked to programmer 24 and the control signals for the telemetry circuit within telemetry module 88, e.g., via an address/data bus. In some examples, telemetry module 88 may provide received data to processor 80 via a multiplexer.

In some examples, processor 80 may transmit atrial and ventricular heart signals (e.g., electrocardiogram signals) produced by atrial and ventricular sense amp circuits within sensing module 86 to programmer 24. Programmer 24 may interrogate IMD 16 to receive the heart signals. Processor 80 may store heart signals within memory 82, and retrieve stored heart signals from memory 82. Processor 80 may also generate and store marker codes indicative of different cardiac events that sensing module 86 detects, and transmit the marker codes to programmer 24. An example pacemaker with marker-channel capability is described in U.S. Pat. No. 4,374,382 to Markowitz, entitled, "MARKER CHANNEL TELEMETRY SYSTEM FOR A MEDICAL DEVICE," which issued on Feb. 15, 1983 and is incorporated herein by reference in its entirety.

The various components of IMD 16 are coupled to power source 90, which may include a rechargeable or non-rechargeable battery. A non-rechargeable battery may be capable of holding a charge for several years, while a rechargeable battery may be inductively charged from an external device, e.g., on a daily or weekly basis.

Figure 4:
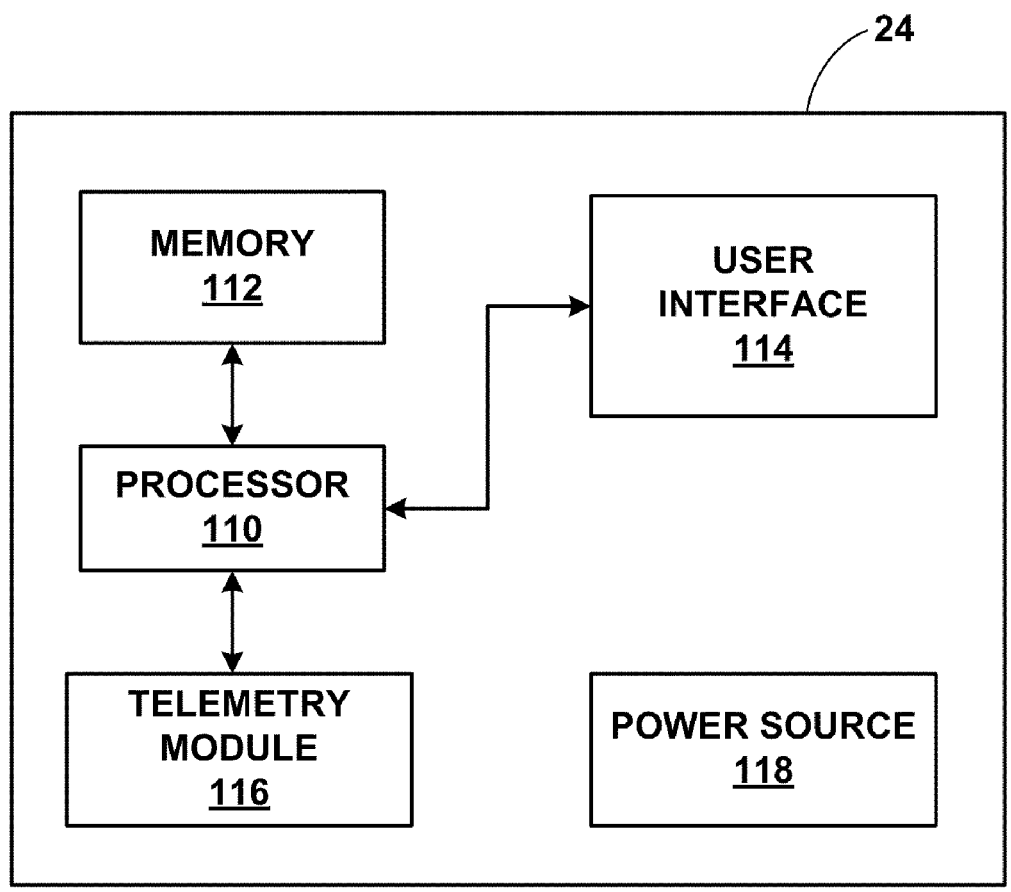
FIG. 4 is a functional block diagram illustrating an example configuration of an external programmer that facilitates user communication with the IMD.

FIG. 4 is functional block diagram illustrating an example configuration of programmer 24. As shown in FIG. 4, programmer 24 may include a processor 110, memory 112, user interface 114, telemetry module 116, and power source 118. Programmer 24 may be a dedicated hardware device with dedicated software for programming of IMD 16. Alternatively, programmer 24 may be an off-the-shelf computing device running an application that enables programmer 24 to program IMD 16.

A user may use programmer 24 to select therapy programs (e.g., sets of stimulation parameters), generate new therapy programs, modify therapy programs through individual or global adjustments or transmit the new programs to a medical device, such as IMD 16 (FIG. 1). The clinician may interact with programmer 24 via user interface 114, which may include display to present graphical user interface to a user, and a keypad or another mechanism for receiving input from a user.

Processor 110 can take the form one or more microprocessors, DSPs, ASICs, FPGAs, programmable logic circuitry, or the like, and the functions attributed to processor 110 herein may be embodied as hardware, firmware, software or any combination thereof. Memory 112 may store instructions that cause processor 110 to provide the functionality ascribed to programmer 24 herein, and information used by processor 110 to provide the functionality ascribed to programmer 24 herein. Memory 112 may include any fixed or removable magnetic, optical, or electrical media, such as RAM, ROM, CD-ROM, hard or floppy magnetic disks, EEPROM, or the like. Memory 112 may also include a removable memory portion that may be used to provide memory updates or increases in memory capacities. A removable memory may also allow patient data to be easily transferred to another computing device, or to be removed before programmer 24 is used to program therapy for another patient.

Programmer 24 may communicate wirelessly with IMD 16, such as using RF communication or proximal inductive interaction. This wireless communication is possible through the use of telemetry module 116, which may be coupled to an internal antenna or an external antenna. An external antenna that is coupled to programmer 24 may correspond to the programming head that may be placed over heart 12, as described above with reference to FIG. 1. Telemetry module 116 may be similar to telemetry module 88 of IMD 16 (FIG. 3).

Telemetry module 116 may also be configured to communicate with another computing device via wireless communication techniques, or direct communication through a wired connection. Examples of local wireless communication techniques that may be employed to facilitate communication between programmer 24 and another computing device include RF communication according to the 802.11 or Bluetooth specification sets, infrared communication, e.g., according to the IrDA standard, or other standard or proprietary telemetry protocols. In this manner, other external devices may be capable of communicating with programmer 24 without needing to establish a secure wireless connection. An additional computing device in communication with programmer 24 may be a networked device such as a server capable of processing information retrieved from IMD 16.

Power source 118 delivers operating power to the components of programmer 24. Power source 118 may include a battery and a power generation circuit to produce the operating power. In some embodiments, the battery may be rechargeable to allow extended operation. Recharging may be accomplished by electrically coupling power source 118 to a cradle or plug that is connected to an alternating current (AC) outlet. In addition or alternatively, recharging may be accomplished through proximal inductive interaction between an external charger and an inductive charging coil within programmer 24. In other embodiments, traditional batteries (e.g., nickel cadmium or lithium ion batteries) may be used. In addition, programmer 24 may be directly coupled to an alternating current outlet to power programmer 24. Power source 118 may include circuitry to monitor power remaining within a battery. In this manner, user interface 114 may provide a current battery level indicator or low battery level indicator when the battery needs to be replaced or recharged. In some cases, power source 118 may be capable of estimating the remaining time of operation using the current battery.

Figure 5:
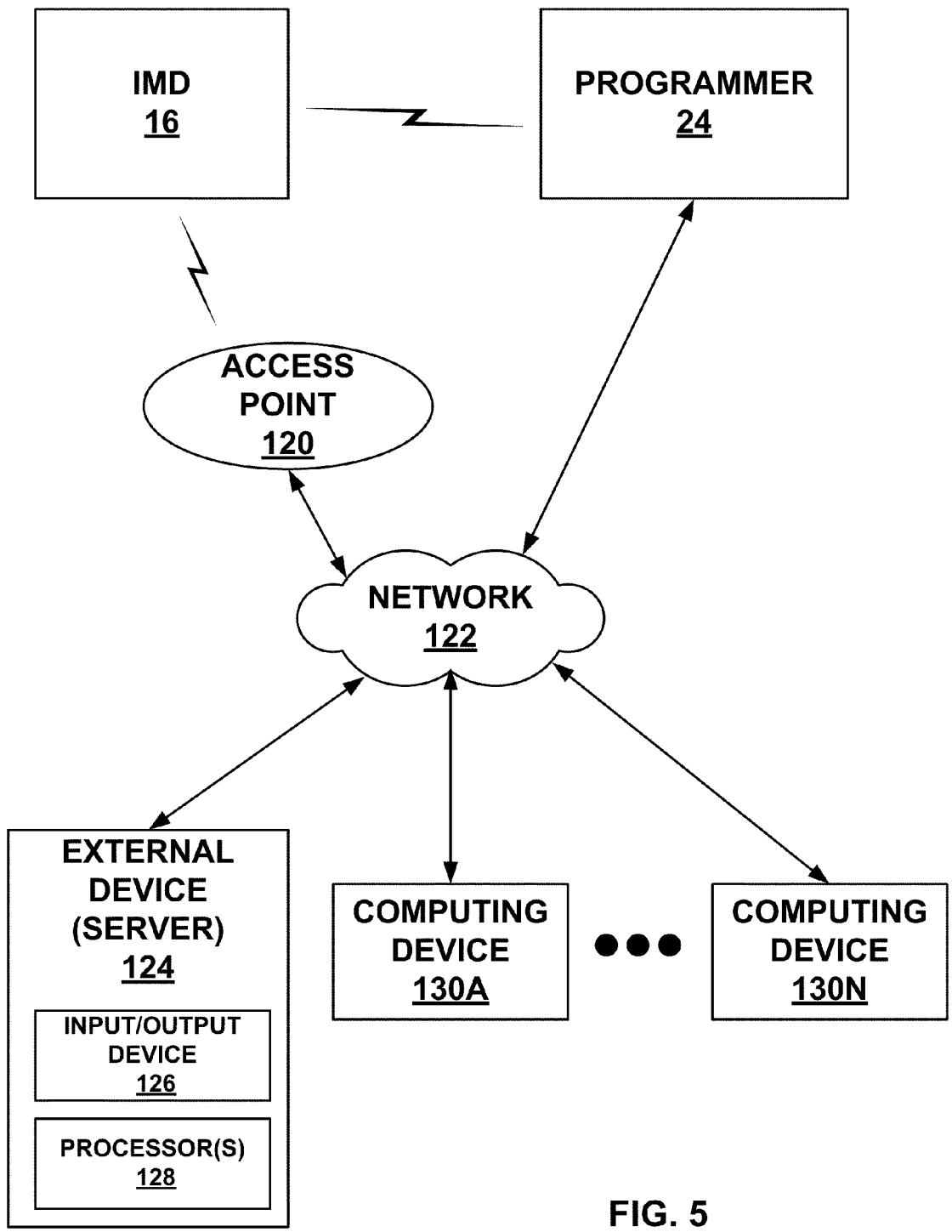
FIG. 5 is a block diagram illustrating an example system that includes an external device, such as a server, and one or more computing devices that are coupled to the IMD and programmer shown in FIG. 1 via a network.

FIG. 5 is a block diagram illustrating an example system that includes an external device, such as a server 124, and one or more computing devices 130A-130N, that are coupled to the IMD 16 and programmer 24 shown in FIG. 1 via a network 122. In this example, IMD 16 may use its telemetry module 88 to communicate with programmer 24 via a first wireless connection, and to communication with an access point 120 via a second wireless connection. In the example of FIG. 5, access point 120, programmer 24, server 124, and computing devices 130A-130N are interconnected, and able to communicate with each other, through network 122. In some cases, one or more of access point 120, programmer 24, server 124, and computing devices 130A-130N may be coupled to network 122 through one or more wireless connections. IMD 16, programmer 24, server 124, and computing devices 130A-130N may each comprise one or more processors, such as one or more microprocessors, DSPs, ASICs, FPGAs, programmable logic circuitry, or the like, that may perform various functions and operations, such as those described herein.

Access point 120 may comprise a device that connects to network 122 via any of a variety of connections, such as telephone dial-up, digital subscriber line (DSL), or cable modem connections. In other embodiments, access point 120 may be coupled to network 122 through different forms of connections, including wired or wireless connections. In some embodiments, access point 120 may be co-located with patient 14 and may comprise one or more programming units and/or computing devices (e.g., one or more monitoring units) that may perform various functions and operations described herein. For example, access point 120 may include a home-monitoring unit that is co-located with patient 14 and that may monitor the activity of IMD 16.

In some examples, server 124 or computing devices 130 may perform any of the various functions or operations described herein. As shown in FIG. 5, server 124 may include an input/output device 126 and processors 128, similar to programmer 24. A user may interact with server 124 via input/output device 126, similar to programmer 24. In addition, processors 128 may perform any calculations, data processing, communication relay, or any other task required to treat or monitor patient 14.

Network 122 may comprise a local area network, wide area network, or global network, such as the Internet. In some cases, programmer 24 or server 124 may assemble sensing integrity information in web pages or other documents for viewing by and trained professionals, such as clinicians, via viewing terminals associated with computing devices 130A-130N. The system of FIG. 5 may be implemented, in some aspects, with general network technology and functionality similar to that provided by the Medtronic CareLink® Network developed by Medtronic, Inc., of Minneapolis, Minn.

FIG. 6A is schematic illustration of delivery catheter 150 arranged in primary vein (or vessel) 152 of coronary sinus 30 of patient 14. Delivery catheter 150 is a bilumenal catheter including first lumen 154, second lumen 156, inflatable member 158, contoured region 160, and aperture 162. A guide member, e.g., guide wire 164 and sheath 166 are received within first lumen 154. Inflatable member 158 is connected to and configured to be inflated by second lumen 156. Inflatable member 158 is connected to second lumen 156 toward distal end 150a of catheter 150. First lumen 154 terminates at aperture 162 included in the exterior surface of catheter 150 toward a proximal end of inflatable member 158.

In practice, catheter 150 is arranged in coronary sinus 30 of heart 12 by guiding the catheter through, e.g., one or more veins and the superior vena cava into right atrium 26, and into primary vein 152 of the coronary sinus. Catheter 150 includes contoured region 160 toward distal end 150a. Contoured region 160 is shaped to assist in turning catheter 150 from inside right atrium 26 into coronary sinus 30. The shape of contoured region 160 shown in FIG. 6A is illustrative. In other examples, the shape of contoured region 160 of catheter 150 may be varied to assist clinicians in guiding the catheter to a region adjacent a target implantation location such that inflatable member 158 may be employed to deflect an implantable medical device toward the target implantation location. For example, contoured region 160, instead of the curved shape shown in FIG. 6A, may include a "J" or hook shape. In one example, contoured region 160 of catheter 150 includes a "C" shape.

After catheter 150 is guided into primary vein 152 of coronary sinus 30, inflatable member 158 is actuated with a gas including, e.g., air delivered under pressure through second lumen 156. Inflatable member may also, in other examples, be actuated by delivering a fluid through second lumen 156 including, e.g., delivering saline, a contrast medium, or combinations thereof. When inflated, inflatable member 158 may act to anchor or otherwise secure catheter 150 at a desired location within primary vein 152. Sheath 166, in which guide wire 164 is arranged, is inserted and advanced into and through first lumen 154. First lumen 154 terminates proximate the proximal end of inflatable member 158 adjacent to or at aperture 162. Sheath 166 is advanced through first lumen 154 and aperture 162 to engage the shoulder of inflatable member 158, causing sheath 166 to turn toward secondary vein 168. Sheath 166 may be employed as shown in FIG. 6A to provide a blunter element, relative to guide wire 164, to be deflected by inflatable member 158. Additionally, sheath 166 may guard the distal end of guide wire 164 to prevent the guide wire from piercing inflatable member 158. After inflatable member 158 deflects sheath 166 toward secondary vein 168, guide wire 164 is advanced out of sheath 166 and into secondary vein 168 of coronary sinus 30. In some examples, sheath 166 is removed, inflatable member 158 is deflated, and catheter 150 is removed, leaving guide wire 164 in place in secondary vein 168 of coronary sinus 30. LV lead 20 is guided along guide wire 164 and into vein 168. Thereafter, guide wire 164 is removed.

FIG. 6B illustrates angle A of secondary vein 168 with respect to longitudinal axis 169 of primary vein 152 of coronary sinus 30. For clarity, delivery catheter 160 is omitted from FIG. 6B. Subselecting vessels off of primary vein 152 of coronary sinus 30 is often difficult because the take-off angle of the vessels from the primary vein is often severe. It is not uncommon, e.g., for a vessel, e.g. secondary vein 168 branching off of primary vein 152 of coronary sinus 30 to have a take-off angle A in a range from 60 to more than 90 degrees with respect to longitudinal axis 169 of the coronary sinus.

Inflatable member 158 includes, e.g., a balloon comprising a material selected from the group consisting of silicone, polyurethane, silicone-urethane co-polymer, cis-1,4 polyisoprene, natural rubber latex, nitrile rubber, butyl rubber, SIBS elastomer, SIS elastomer, and combinations thereof. Inflatable member 158 may be tuned to deflect implantable medical devices, e.g. lead 20, guide wire 164, and/or sheath 166, at different angles with respect to the path along which catheter 150 lies. Increasing or decreasing the pressure of gas (or the amount of liquid) in inflatable member 158 will vary the size of the member, which, in turn, will proportionately increase or decrease the angle that, e.g., sheath 166 is deflected.

In some examples, arranging catheter 150 properly within primary vein 152 of coronary sinus 30 may be assisted by one or more opaque markers viewable with fluoroscopic techniques or with an irrigated lumen that dispenses contrast media to assist in imaging the relative positions of, e.g., aperture 162 and secondary vein 168. Additionally, inflatable member 158 may, in addition to or in lieu of deflecting sheath 166, be inflated to cause the outside walls of catheter 150 to occlude primary vein 152, or another vessel in which catheter 150 is arranged. After occluding vein 152 by expanding inflatable member 158, a dye may be injected, e.g. from distal end 156a of second lumen 156 into vein 152. The injected dye may be employed in, e.g., various venography procedures. In one example, inflatable member 158 is expanded to cause catheter 150 to occlude primary vein 152 of coronary sinus 30. A venogram dye is delivered through distal end 156a of second lumen 156 and distal end 150a of catheter 150 into vein 152. A venogram is generated of vein 152 and its branching vessels including secondary vein 168 to facilitate placing lead 20 in vein 166. For example, the venogram is employed to arrange catheter 150 in primary vein 152 such that aperture 162 is adjacent to and pointed toward secondary vein 168.

FIGS. 7A and 7B and 8A and 8B show two additional examples, respectively, of catheters configured to deflect an implantable medical device in order to subselect vessels or other cavities, passages, or the like within the body of patient 14. In the examples of FIGS. 7A-8B, an inflatable member forms a portion of the outer longitudinal surface of the catheter such that the inflatable member, when actuated, acts to deflect the delivery catheter itself, which in turn necessarily deflects the device(s) arranged therein.

FIGS. 7A and 7B are schematic illustrations of bilumenal catheter 170 including first lumen 174, second lumen 176, and inflatable member 178. Guide wire 179 is received within first lumen 174. Inflatable member 178 is connected to and configured to be inflated by second lumen 176. Inflatable member 178 forms a portion of outer surface 170b of catheter 170 toward distal end 170a. In this manner, inflatable member 178 is expandable to asymmetrically elongate outer surface 170b of catheter 170, which, in turn, causes distal end 170a of catheter 170 to deflect.

As described with reference to the example of FIG. 6A, inflatable member 178 includes, e.g., a balloon comprising silicone, polyurethane, silicone-urethane co-polymer, cis-1,4 polyisoprene, natural rubber latex, nitrile rubber, butyl rubber, SIBS elastomer, SIS elastomer, or combinations thereof. Inflatable member 178 may be tuned to deflect distal end 170a of catheter 170 at different angles. Increasing or decreasing the pressure of gas (or the amount of liquid) in inflatable member 178 will vary the size of the member which, in turn, will proportionately increase or decrease the angle that, e.g., catheter 170 is deflected.

Inflatable member 178 is actuated with a gas including, e.g., air delivered under pressure through second lumen 176. Inflatable member 178 may also, in other examples, be actuated by delivering a fluid through second lumen 176 including, e.g., delivering saline, a contrast medium, or combinations thereof. Inflatable member 178 expands from a first size in FIG. 7A to a second larger size in FIG. 7B. As inflatable member 178 expands, portion 178a that forms part of outer surface 170b of catheter 170 changes from a first size in FIG. 7A to a second size larger than the first size in FIG. 7B. In this manner, inflatable member 178 asymmetrically elongates outer surface 170b of catheter 170, which, in turn, causes distal end 170a of catheter 170 including first lumen 174 to deflect, as shown in FIG. 7B. After deflecting distal end 170a of catheter 170, guide wire 179 is advanced through deflected first lumen 174 toward distal end 170a of catheter 170. Guide wire 179 is advanced out of first lumen 174 through distal end 170a of catheter 170 into, e.g., secondary vein 168 of coronary sinus 30 (not shown in FIGS. 7A and 7B). In some examples, inflatable member 178 is deflated and catheter 170 is removed, leaving guide wire 179 in place in secondary vein 168 of coronary sinus 30. LV lead 20 is guided along guide wire 179 and into vein 168. Thereafter, guide wire 179 is removed.

FIGS. 8A and 8B are schematic illustrations of bilumenal catheter 180 including first lumen 184, second lumen 186, and inflatable member 188. Guide wire 189 is received within first lumen 184. Inflatable member 188 is connected to and configured to be inflated by second lumen 186. As with the example of FIGS. 7A and 7B, inflatable member 188 forms a portion of outer surface 180b of catheter 180 toward distal end 180a. In this manner, inflatable member 188 is expandable to asymmetrically elongate outer surface 180b of catheter 180, which, in turn, causes distal end 180a of catheter 180 to deflect.

In contrast to the example of FIGS. 6A and 7A and 7B, inflatable member 188 includes bellows member comprising, e.g., silicone, polyurethane, silicone-urethane co-polymer, cis-1,4 polyisoprene, natural rubber latex, nitrile rubber, butyl rubber, SIBS elastomer, SIS elastomer, or combinations thereof. Similar to the foregoing examples, inflatable member 188 may be tuned to deflect distal end 180a of catheter 180 at different angles. Increasing or decreasing the pressure of gas (or the amount of liquid) in inflatable member 188 will vary the size of the member, which, in turn, will proportionately increase or decrease the angle that, e.g., catheter 180 is deflected. However, the bellows configuration of inflatable member 188 restricts the expansion of the element primarily to the longitudinal direction, which may act to reduce the transverse size of catheter 180 when inflatable member 188 is expanded.

In any event, as with inflatable member 158, inflatable member 188 is actuated with a gas including, e.g., air delivered under pressure through second lumen 186. Inflatable member 188 may also, in other examples, be actuated by delivering a fluid through second lumen 186 including, e.g., delivering saline, a contrast medium, or combinations thereof. Inflatable member 188 expands from a first size in FIG. 8A to a second larger size in FIG. 8B. As inflatable member 188 expands, portion 188a that forms part of outer surface 180b of catheter 180 changes from a first size in FIG. 8A to a second size larger than the first size in FIG. 8B. In this manner, inflatable member 188 asymmetrically elongates outer surface 180b of catheter 180, which, in turn, causes distal end 180a of catheter 180 including first lumen 184 to deflect, as shown in FIG. 8B. After deflecting distal end 180a of catheter 180, guide wire 189 is advanced through deflected first lumen 184 toward distal end 180a of catheter 180. Guide wire 189 is advanced out of first lumen 184 through distal end 180a of catheter 180 into, e.g., secondary vein 168 of coronary sinus 30 (not shown in FIGS. 8A and 8B). In some examples, inflatable member 188 is deflated and catheter 180 is removed, leaving guide wire 189 in place in secondary vein 168 of coronary sinus 30. LV lead 20 is guided along guide wire 189 and into vein 168. Thereafter, guide wire 189 is removed.

In the examples of FIGS. 7A and 7B, and 8A and 8B, the delivery catheter employed therein is capable of making multiple subselections. With reference to biluminal delivery catheter 170, for example, after making a first subselection as described above, instead of deploying guide wire 179 and removing catheter 170, guide wire 179 is advanced out of first lumen 184 through distal end 180a of catheter 180 into the first subselected vessel. After advancing guide wire 179 into the vessel, inflatable member 178 may be deflated and catheter 170 may be further advanced along guide wire 179 into and through the first subselected vessel to a second vessel. After reaching the second vessel from the first subselected vessel, catheter 170 and inflatable member 178 may be employed in the same fashion as with the subselection of the first vessel to subselect the second vessel. In particular, inflatable member 178 is actuated with a gas or liquid delivered through second lumen 176 and expands from a first size in FIG. 7A to a second larger size in FIG. 7B. As inflatable member 178 expands, portion 178a that forms part of outer surface 170b of catheter 170 changes from a first size in FIG. 7A to a second size larger than the first size in FIG. 7B. In this manner, inflatable member 178 asymmetrically elongates outer surface 170b of catheter 170, which, in turn, causes distal end 170a of catheter 170 including first lumen 174 to deflect, as shown in FIG. 7B. After deflecting distal end 170a of catheter 170, guide wire 179 is advanced into the second subselected vessel. Inflatable member 178 may be deflated and catheter 170 removed, leaving guide wire 179 in place in the second vessel. A medical lead, e.g., LV lead 20 may then be guided along guide wire 179 through the first subselected vessel and into the second subselected vessel. Thereafter, guide wire 179 is removed.

In addition to making multiple subselections with either of the examples of FIGS. 7A and 7B, and 8A and 8B, either of these examples may be combined with the example of FIGS. 6A and 6B to make multiple subselections. With reference to FIGS. 7A and 7B, for example, biluminal catheter 170 may be combined with catheter 150 of FIGS. 6A and 6B to make a first subselection by deflecting distal end 170a of catheter 170 with inflatable member 178 and advancing the distal end of the catheter into a first subselected vessel. A second subselection may then be made by deflecting a medical device, e.g. guide wire 164 and/or sheath 166 with inflatable member 158 as the guide wire and/or sheath are advanced from the catheter, e.g., via aperture 162 to turn the guide wire and/or sheath into a second subselected vessel from the first subselected vessel.

In some examples, first lumen 154 in which guide wire 164 and sheath 166 are arranged may employed for both subselections, so first lumen 154 would have a distal exit port at the distal end of the catheter, e.g. distal end 170a of catheter 170 of FIGS. 7A and 7B, and a side exit port, e.g. aperture 162 in catheter 160 of FIG. 6A, proximal to an inflatable member off of which guide wire 164 and/or sheath 166 are deflected for the second subselection. In this case, the catheter would require a mechanism to enable each of the distal and side exit port to be selected. In one example, sheath 166 of FIG. 6A may be configured biased into a predetermined curved shape. In order to access the distal exit port, sheath 166 is prearranged within first lumen 154 distal to the side exit port, thus preventing access to the side exit and allowing sheath 166 and guide wire 164 to be advanced out of the distal exit port. In order to access the side exit port, the distal end of sheath 166 is retracted back past the side exit port, i.e. in a direction toward the proximal end of the catheter, so that the biased curved shape of the sheath is released out of first lumen 154 to snap toward the side exit port. Sheath 166 and guide wire 164 may then be advanced out of the side exit port.

Figure 9:
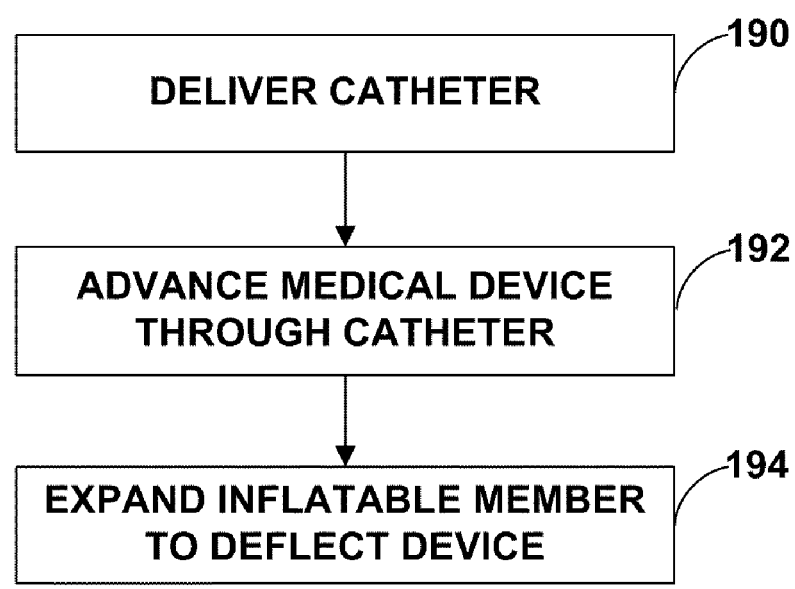
FIG. 9 is a flowchart illustrating an example method of placing an implantable medical device.

FIG. 9 is a flowchart illustrating an example method of placing an implantable medical device including, e.g., placing LV lead 20 in a secondary vein of coronary sinus 30 of heart 12. The example method of FIG. 10 generally includes delivering a catheter including an inflatable member through a vessel within a patient (180), advancing a medical device through the catheter (182), and expanding the inflatable member to deflect the medical device at an acute angle with respect to a longitudinal axis of the vessel (184).

The method illustrated in FIG. 9 includes delivering a catheter including an inflatable member through a vessel within a patient (180). In some examples, catheter 150 is delivered into coronary sinus 30 of heart 12 by guiding the catheter through, e.g., one or more veins and the superior vena cava into right atrium 26, and into primary vein 152 of the coronary sinus. Catheter 150 may include a contoured region the distal end of the catheter that is shaped to assist in turning catheter 150 from inside right atrium 26 into coronary sinus 30. The shape of contoured region may be varied to assist clinicians in guiding the catheter to a region adjacent a target implantation location such that inflatable member 158 may be employed to deflect an implantable medical device toward the target implantation location. For example, catheter 150 may include a contoured region with a curved shape as shown in FIG. 6A. In another example, catheter 150 includes a contoured region with a "J" or hook shape. In one more example, a contoured region of catheter 150 includes a "C" shape.

The method of FIG. 9 also includes advancing an implantable medical device through the catheter (182) and expanding the inflatable member to deflect the medical device at an acute angle with respect to a longitudinal axis of the vessel (184), e.g. axis 169 of primary vein 152 of coronary sinus 30 shown in FIG. 6B. As explained above with reference to FIG. 6A, and FIGS. 7A, 7B and 8A, 8B respectively, catheter 150 may include an inflatable member, e.g. inflatable member 158 that, when actuated, acts to deflect a device received within the catheter in order to direct the device out of an aperture in the catheter, and thereby into the secondary vein 168 that branches off of primary vein 152 of coronary sinus 30. In other examples, an inflatable member, e.g. inflatable member 178 or 188, acts to deflect catheter 150 itself, which in turn necessarily deflects the medical device arranged therein. In one example including inflatable member 158 that acts to deflect a device received within catheter 150 in order to direct the device out of aperture 162 in the catheter, sheath 166, in which guide wire 164 is arranged, is inserted and advanced into and through first lumen 154 of catheter 150. First lumen 154 terminates proximate aperture 162. Sheath 166 is advanced through and out of aperture 162 to engage the shoulder of inflatable member 158, causing sheath 166 to turn toward secondary vein 168.

Inflatable member 158, 178, or 188, e.g., may be actuated with a gas including, e.g., air delivered under pressure through second lumen 156 of catheter 150. In another example, inflatable member 158 is actuated by delivering a fluid through second lumen 156 including, e.g., delivering saline, a contrast medium, or combinations thereof. In some examples, inflatable member 158 may, in addition to or in lieu of deflecting a medical device, be inflated to occlude primary vein 152, or another vessel in which catheter 150 is arranged. After occluding vein 152 by expanding inflatable member 158, a dye may be injected, e.g. from distal end 156a of second lumen 156 into vein 152. The injected dye may be employed in, e.g., various venography procedures. In one example, inflatable member 158 is expanded to cause catheter 150 to occlude primary vein 152 of coronary sinus 30. A venogram dye is delivered through distal end 156a of second lumen 156 and distal end 150a of catheter 150 into vein 152. A venogram is generated of vein 152 and its branching vessels including secondary vein 168 to facilitate placing lead 20 in vein 166. For example, the venogram is employed to reposition catheter 150 in primary vein 152 after initially delivering the catheter (180) such that aperture 162 is adjacent to and pointed toward secondary vein 168. After generating the venogram and properly positioning catheter 150 in vein 152, inflatable member 158 is at least partially deflated such that catheter 150 no longer completely occludes the primary vein of coronary sinus 30.

After inflatable member 158 is expanded to deflect sheath 166 toward secondary vein 168, guide wire 164 is advanced out of sheath 166 through aperture 162 into the secondary vein of coronary sinus 30. In some examples, inflatable member 158 is deflated and catheter 150 is removed, leaving guide wire 164 in place in secondary vein 168 of coronary sinus 30. LV lead 20 is guided along guide wire 164 and into vein 168. Thereafter, guide wire 164 is removed.

The techniques disclosed herein may provide several advantages over past systems and methods for placing implantable medical devices in vessels or other cavities, passages, or the like within a patient's body. In particular, the disclosed examples provide techniques for delivering medical devices, e.g. an implantable medical lead or a drug pump catheter, via a delivery catheter capable of subselecting vessels or other cavities, passages, or the like within a patient's body using an inflatable member that deflects the implantable medical device away from the path along which the catheter is arranged. The foregoing examples facilitate placement of various medical devices within a patient's body along a path that includes a multitude of twists and turns within vessels or other parts of the body. The precise placement of, e.g., an implantable medical lead in a small vessel branching off of another more accessible vessel may be necessary in order to, e.g., avoid unintentional and/or undesirable stimulation of nerves or other tissue that lie adjacent or otherwise in the region of a target stimulation location. The techniques described above allow a clinician to subselect vessels off of a primary vessel that take-off of the primary vessel at relatively sever angles.

Various examples have been described. These and other examples are within the scope of the invention defined by the following claims.

The invention claimed is:

1. A method comprising:
   delivering a catheter comprising an inflatable member arranged on a distal portion of the delivery catheter through a primary vein of a coronary sinus of a patient;
   advancing a medical device through the catheter; and
   expanding the inflatable member to deflect the medical device from the primary vein into a secondary vein of the coronary sinus, wherein expanding the inflatable member to deflect the medical device comprises deflecting the medical device off of the inflatable member toward the secondary vein of the coronary sinus.

2. The method of claim 1, wherein expanding the inflatable member comprises expanding the inflatable member to occlude the primary vein.

3. The method of claim 2, further comprising injecting a dye through the catheter into the primary vein.

4. The method of claim 3, wherein the dye comprises a venogram dye.

5. The method of claim 4, further comprising generating a venogram of the primary vein and the catheter arranged therein.

6. The method of claim 5, further comprising repositioning the catheter within the primary vein based on the venogram.

7. The method of claim 6, further comprising at least partially deflating the inflatable member.

* * * * *